United States Patent [19]
Freschi

[11] Patent Number: 5,853,390
[45] Date of Patent: Dec. 29, 1998

[54] SYRINGE FOR HYPODERMIC INJECTIONS

[75] Inventor: Claudio Freschi, Forlì', Italy

[73] Assignee: Giovanni Freschi, Forlì', Italy

[21] Appl. No.: 743,035

[22] Filed: Nov. 4, 1996

[30] Foreign Application Priority Data

Nov. 10, 1995 [IT] Italy .............. BO95 A 000533

[51] Int. Cl.$^6$ .................................................. A61M 5/00
[52] U.S. Cl. .......................................................... 604/110
[58] Field of Search ................................ 604/110, 181, 604/187, 195, 198, 218, 228; 128/919

[56] References Cited

U.S. PATENT DOCUMENTS

| | | | |
|---|---|---|---|
| 4,973,316 | 11/1990 | Dysarz | 604/195 |
| 5,049,133 | 9/1991 | Villen Pascual | 604/110 |
| 5,064,419 | 11/1991 | Gaarde | 604/195 |
| 5,114,410 | 5/1992 | Caralt Batlle | 604/195 |
| 5,190,526 | 3/1993 | Murray et al. | 604/110 |
| 5,211,629 | 5/1993 | Pressly et al. | 604/110 |

*Primary Examiner*—Wynn Wood Coggins
*Assistant Examiner*—Deborah Blyveis
*Attorney, Agent, or Firm*—Guido Modiano; Albert Josif

[57] ABSTRACT

A syringe for hypodermic injections comprising a cylindrical body inside which a plunger is fitted so as to be slideable and actuatable by means of a stem that protrudes from an open end of the cylindrical body. An internally hollow needle is associated with the opposite end of the cylindrical body and is adapted to retract inside the cylindrical body, actuated by an elastic element, at the end of the injection.

7 Claims, 1 Drawing Sheet

SYRINGE FOR HYPODERMIC INJECTIONS

BACKGROUND OF THE INVENTION

The present invention relates to a syringe for hypodermic injections.

It is known that syringes for hypodermic injections are usually constituted by a cylindrical body inside which a plunger is slidingly fitted, the plunger being actuatable by means of a stem that protrudes from an open end of said cylindrical body. An internally hollow needle is associated with the opposite end of said cylindrical body.

Use of disposable syringes, made of plastics and meant to be discarded after use, is currently widespread. This of course avoids resorting to sterilization, which is instead required with conventional glass syringes, since disposable syringes are supplied in a sterile package.

A considerable problem linked to the use of said syringes is the risk of infections that arises after use in case of accidental puncture with a dirty needle. The needle of the syringes in fact makes contact with the blood of the patient and is therefore a vehicle for possible infections if said blood is infected.

It should be noted that infections which can be transmitted in this manner often correspond to very severe disorders.

Moreover, used syringes are sometimes discarded without any precaution, for example in public places such as parks and the like. This is obviously a very severe danger for people who visit these public places.

SUMMARY OF THE INVENTION

A principal aim of the present invention is to solve the above problem, by providing a syringe for hypodermic injections that is capable of avoiding the risk of accidental punctures after said syringe has been used.

Within the scope of this aim, an object of the present invention is to provide a syringe that is simple in concept, safely reliable in operation, and has a relatively low cost.

This aim and this object are both achieved, according to the invention, by the present syringe for hypodermic injections, comprising: a cylindrical body; a plunger that is fitted so as to be slideable inside said cylindrical body and actuatable by means of a stem that protrudes from an open end of said cylindrical body; and an internally hollow needle that is associated with the opposite end of said cylindrical body, wherein said needle is adapted to retract inside said cylindrical body, actuated by elastic means, at the end of the injection.

BRIEF DESCRIPTION OF THE DRAWINGS

Further characteristics and advantages of the invention will become apparent from the following detailed description of a preferred embodiment of the syringe for hypodermic injections, illustrated only by way of non-limitative example in the accompanying drawings, wherein.

DESCRIPTION OF THE PREFERRED EMBODIMENTS

Figure 1:
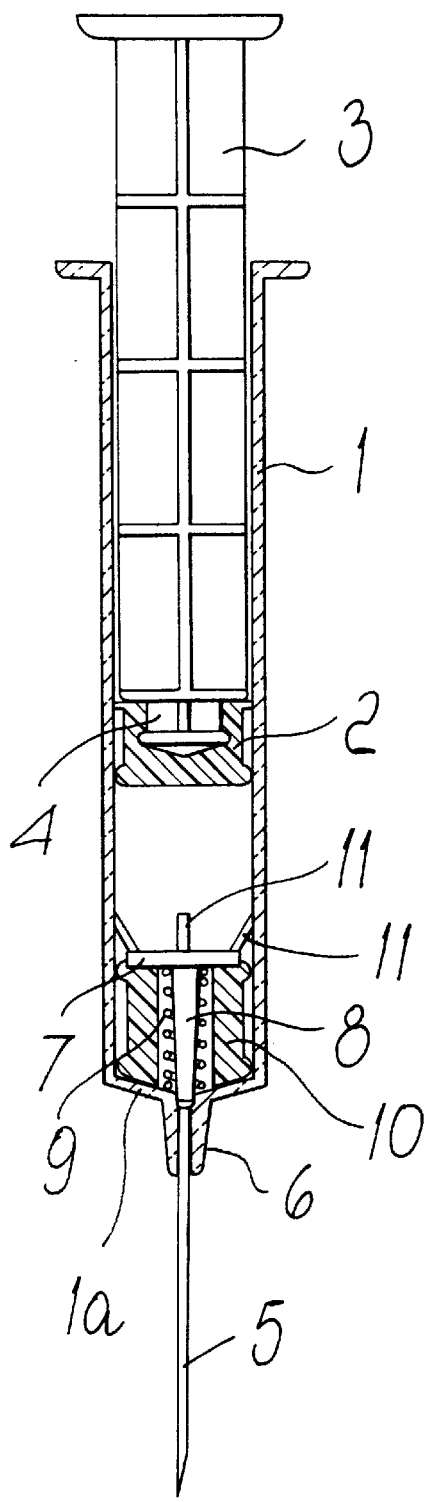
FIG. 1 is a general longitudinal sectional view of the syringe according to the invention.
Figure 2:
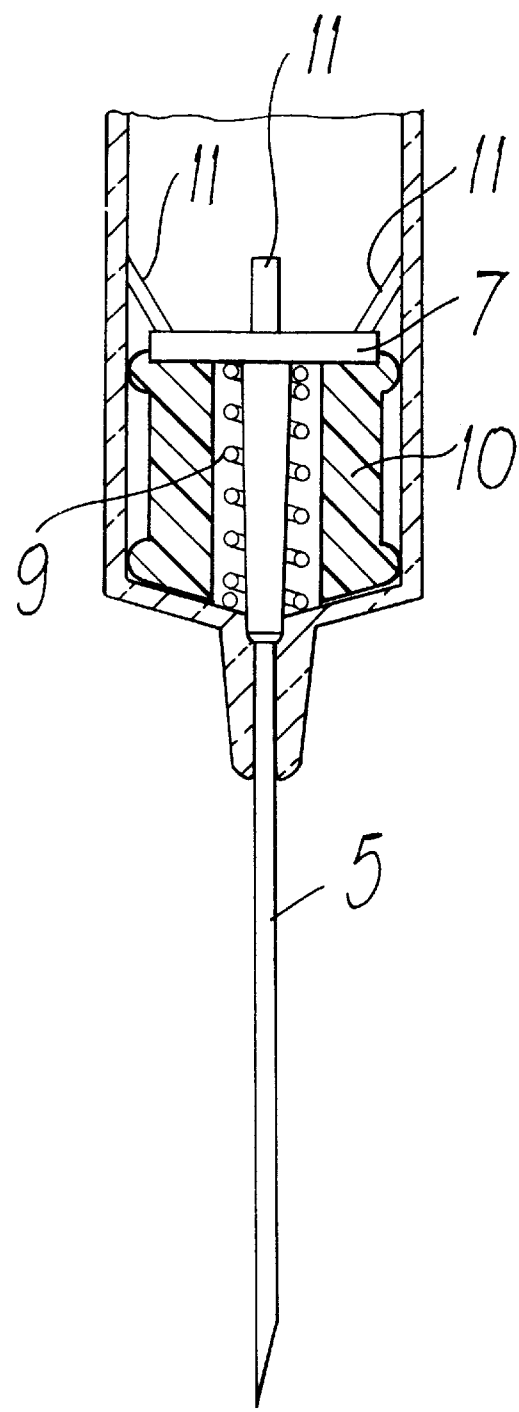
FIG. 2 is an enlarged-scale view of a detail of FIG. 1.

With particular reference to the above figures, the reference numeral 1 designates the tubular cylindrical body of the syringe for hypodermic injections, which is preferably made of transparent plastics.

A plunger 2 is slidingly fitted inside the cylindrical body 1 and can be actuated by means of a stem 3 that protrudes from the open rear end of said cylindrical body 1; the stem 3 is axially rigidly coupled to the plunger 2 by means of a tang 4 that is push-fitted in a corresponding rear cavity of said plunger.

The plunger 2 forms lips, through which it provides a seal on the inner surface of the cylindrical body 1.

An internally hollow needle 5 is associated with the front end of the cylindrical body 1 of the syringe and passes, so that it can slide freely, through a sleeve 6 that is formed axially by said cylindrical body 1 at the bottom 1a.

The needle 5 is provided, at the rear, with a disk 7 arranged on a plane lying transversely to the longitudinal axis; the disk 7 is provided with a stem 8 made of plastic material that is applied to the needle 5.

The needle 5 is actuated elastically by a helical spring 9 that acts by compression between the bottom 1a of the cylindrical body 1 and the disk 7. The spring 9 is guided on the stem 8 of the needle 5 and is inserted in the cavity of a tubular head 10 that is fitted inside the cylindrical body 1 in abutment against the bottom 1a. More specifically, the head 10, made of a material such as rubber, forms a sort of spool that is inserted hermetically at the bottom of the cylindrical body 1.

The disk 7 is kept normally in contact against the head 10, in contrast with the elastic action of the spring 9, by means of a plurality of flexible tabs 11 that protrude from the internal surface of the cylindrical body 1. The tabs 11, which are distributed uniformly in a circumferential pattern, converge symmetrically towards the bottom of the syringe, so as to act as a locator for the disk 7; in particular, the tabs 11 are adapted to engage all around the rear face of said disk 7 with their tips. The disk is therefore hermetic against the head 10.

The head 10 may also be formed in said cylindrical body 1 of the syringe and the disk 7 may form a seal thereon by means of a gasket provided in a downward region of said disk.

The operation of the syringe is easily understandable from the above description.

In the operating configuration, the needle 5 is stably coupled to the cylindrical body 1 of the syringe. The disk 7 of the needle is in fact secured between the head 10 of the cylindrical body 1 and the tabs 11 that protrude from said cylindrical body 1.

The syringe is then used in the conventional manner, by acting on the plunger 2, by means of the stem 3, in order to draw the liquid inside the chamber formed by the cylindrical body 1 and then inject said liquid.

At the end of the injection of the liquid, the movement of the plunger 2 opens out the tabs 11. The plunger 2, by engaging the tabs 11, in fact causes their elastic flexing in an outward direction, i.e., against the inner surface of the cylindrical body 1.

When the plunger 2 makes contact with the disk 7, the spacing of the tabs 11 ends and the disk 7 of the needle 5 disengages from said tabs and remains axially actuated by the spring 9. Therefore, the needle 5, being no longer retained by the tabs 11, is pushed by the spring 9 to retract with a snap action inside the cylindrical body 1.

In other words, the needle 5 is retractable inside the cylindrical body 1 of the syringe at the end of the injection. Of course, the size assigned to the components of the syringe is such that said retraction causes the complete reentry of the needle 5 inside the cylindrical body 1.

The syringe is therefore capable of avoiding the risk of accidental punctures after it has been used to perform the hypodermic injection. After use, the needle 5 of the syringe in fact retracts automatically inside the cylindrical body 1. The risk of transmitting infections by means of the syringe is therefore avoided.

It has been found that it is convenient for the spring 9, when not compressed, to be longer than the needle. In this manner, when the needle retracts inside the cylindrical body 1 after the injection, it is arranged transversely and prevents any possible exit.

The fact should also be noted that the syringe according to the invention has a simple structure and is therefore adapted for the production of disposable products meant to be discarded after use.

In the practical execution of the invention, the materials employed, as well as the shapes and the dimensions, may be any according to requirements.

What is claimed is:

1. A syringe for hypodermic injections comprising:

a cylindrical body having a front end, an open rear end, an internal surface and containing a plunger which is axially rigidly coupled to a stem by means of a tang;

a hollow needle connected with said front end of the cylindrical body having a stem and a disk provided at one end of the stem of the needle and arranged on a plane lying transversely to a longitudinal axis of the cylindrical body;

elastic means placed between said front end of the cylindrical body and said disk;

locator means rigidly coupled to the internal surface of said cylindrical body and engaging said disk such that they are actuated by the advancement of said plunger, at the end of the injection, for a snap-action disengagement of the needle;

wherein said needle is adapted to retract inside said cylindrical body, actuated by said elastic means, at the end of the injection.

2. A syringe according to claim 1, wherein said locator means consists of a plurality of flexible tabs that protrude inside said cylindrical body and converge symmetrically towards the front end of the cylindrical body, each of said tabs being provided with a tip which engages said disk.

3. A syringe according to claim 1, wherein said elastic means consists of a helical spring which is guided on the stem of said needle.

4. A syringe according to claim 1, wherein said elastic means is inserted in a cavity of a tubular head that is placed inside said cylindrical body between its front end and the disk.

5. A syringe according to claim 1, wherein said tubular head forms a spool that is hermetically inserted at the front end of the cylindrical body.

6. A syringe according to claim 1, wherein said elastic means is inserted through the axial cavity of said tubular head.

7. A syringe according to claim 1, wherein said needle passes through a sleeve that is formed axially by said cylindrical body.

* * * * *